United States Patent [19]

Speert et al.

[11] Patent Number: 5,441,938
[45] Date of Patent: Aug. 15, 1995

[54] FACTORS WHICH REGULATE MACROPHAGE ANTIBACTERIAL ACTIVITY

[75] Inventors: David Speert; Sameer Barghouthi, both of Vancouver, Canada; Siamon Gordon, Oxford, United Kingdom

[73] Assignee: University of British Columbia, Canada

[21] Appl. No.: 887,496

[22] Filed: May 26, 1992

[51] Int. Cl.⁶ .................... A61K 9/12; A61K 31/70
[52] U.S. Cl. .................................. 514/23; 514/851; 514/853; 514/854; 514/855; 514/888
[58] Field of Search .................. 514/23, 851, 853, 854, 514/855, 888

[56] References Cited

U.S. PATENT DOCUMENTS

| | | | |
|---|---|---|---|
| 3,794,722 | 2/1974 | Taya | 514/814 |
| 4,017,608 | 4/1977 | Gordon | 536/120 |
| 4,061,490 | 12/1977 | Yukinaga et al. | 71/68 |
| 4,158,052 | 6/1979 | Audibert et al. | 424/88 |
| 4,536,398 | 8/1985 | Ito et al. | 514/43 |
| 4,668,508 | 5/1987 | Grollier et al. | 424/70 |
| 4,826,679 | 5/1989 | Roy | 514/851 |
| 5,095,104 | 3/1992 | Gordon | 536/122 |
| 5,100,647 | 3/1992 | Agus et al. | 514/851 |
| 5,157,024 | 10/1992 | Gordon | 514/23 |

OTHER PUBLICATIONS

The Merck Index, Tenth Edition, Windholz, Editor, Published by Merck & Co., Inc. Rathway, N.J., pp. 638, 639 & 819.
Speert, D. P. *Pseudomonas Aeruginosa* Infections in Patients with Cystic Fibrosis in The Natural Immune System, vol. 2, The Macrophage, pp. 217–263, C. E. Lewis and O'D. McGee, Editors, Oxford University Press, 1992.
Michl, J., D. J. Ohlbaum, and S. C. Silverstein, 1976, 2-deoxyglucose selectively inhibits Fc and complement receptor-mediated phagocytosis in mouse peritoneal macrophages. J. Exp. Med. 144:1484–1493.
Speert, D. P. and S. Gordon, 1991, Phagocytosis of Unopsonized *Pseudomonas aeruginosa* by Murine Macrophages is Absolutely Dependent Upon the Presence of Glucose. Abstracts of The 1991 ICAAC.
Speert, D. P. and S. Gordon, 1992. Phagocytosis of Unopsonized *Pseudomonas Aeruginosa* by Murine Macrophages is a Two-Step Process Requiring Glucose. J. Clin. Investigation. in press.

*Primary Examiner*—Ronald W. Griffin
*Attorney, Agent, or Firm*—Lorusso & Loud; Smart & Biggar

[57] ABSTRACT

A novel therapy for *Pseudomonas aeruginosa* infections, in particular in cystic fibrosis patients, is described. Macrophages provide the first line of defence in protecting the lung against bacterial infections. Nonetheless, *Pseudomonas aeruginosa* infections continue to be problematic in cystic fibrosis patients and are the leading cause of death in these patients. Previously, little was known regarding the factors which regulate the capacity of macrophages to mediate phagocytosis of *Pseudomonas aeruginosa*. The inventors have now shown that phagocytosis of nonopsonized *Pseudomonas aeruginosa* by macrophages is dependent upon the presence of glucose. They have also shown that the action of glucose is on the macrophage rather than the bacteria. Glucose therapy can therefore be used to prevent or combat *Pseudomonas aeruginosa* infections.

5 Claims, 4 Drawing Sheets

FACTORS WHICH REGULATE MACROPHAGE ANTIBACTERIAL ACTIVITY

FIELD OF THE INVENTION

The present invention relates to a novel therapy for the treatment or prevention of Pseudomonas aeruginosa infections, in particular in patients with cystic fibrosis.

BACKGROUND OF THE INVENTION

Pseudomonas aeruginosa is the predominant respiratory tract pathogen in patients with cystic fibrosis. Once such patients acquire a Pseudomonas aeruginosa infection, the infection is rarely, if ever, eradicated and a progressive pulmonary deterioration is initiated, ultimately leading to death. In one study, chronic colonization established in the first five years of life was associated with a 20% survival to 16 years of age, whereas 95% of the patients who remained uncolonized in the first five years of life survived to 16 years of age (1). Although the extraordinary predisposition of CF patients to colonization and infection with P. aeruginosa has been recognized for many years, a satisfactory explanation for this phenomenon remains elusive.

Cystic fibrosis is common among caucasians, affecting approximately 1 in 2,000 newborns (2). The mode of inheritance is generally autosomal recessive, suggesting that about 5% of the normal population carries the defective gene. Unfortunately, there are currently no treatments that have resulted in the complete eradication or prevention of Pseudomonas aeruginosa infections in cystic fibrosis patients.

Antimicrobial therapy using antibiotics has been used in several therapeutic protocols. However, the complications that have been observed in antibiotic therapy include the following. Firstly, patients with CF dispose of antimicrobial agents more rapidly than do normal individuals, a phenomenon that mandates therapy with higher doses than those normally recommended. Secondly, strains of Pseudomonas aeruginosa dissociate into multiple phenotypic forms and often with different antimicrobial susceptibility patterns. Thirdly, since the infection is chronic and the infecting strains of Pseudomonas aeruginosa are eradicated rarely, resistance to multiple antimicrobial agents develops frequently. Fourthly, therapeutic levels of antimicrobial agents in sputum are difficult to achieve because of poor penetration and inactivation. Fifthly, the mucoid exopolysaccharide of mucoid strains appears to present a barrier to penetration of some antibiotics. Finally, allergy to certain antibiotics (such as betalactam) renders therapy with antibiotics difficult in some patients.

Anti-inflammatory agents have also been tried in the therapy of Pseudomonas aeruginosa infections in CF patients as it has been postulated that host-mediated inflammation may be responsible for a large part of the pulmonary damage in the CF lung. Efforts have been made to dampen the inflammatory response in the CF lung by use of a systemic steroidal anti-inflammatory therapy using prednisone (3). Unfortunately, prednisone therapy carries substantial risks including growth retardation, glucose intolerance and development of cataracts (4). Preliminary studies are underway to use non-steroidal anti-inflammatory agents.

Therefore, there is a need to provide a therapy for the prevention and eradication of Pseudomonas aeruginosa infections in patients with cystic fibrosis. Therapy to certain diseases has been moving away from classical drug therapy due to adverse drug side effects, to immunotherapies which involve inducing a natural immune response to the pathogen. It is known that phagocytic cells of the immune system (in particular, the lung macrophages) are of critical importance in the host's defence against infections with Pseudomonas aeruginosa. Therefore, it is desirable to understand the mechanism whereby macrophages phagocytose Pseudomonas aeruginosa in order to better understand the dynamics of the host-parasite relationship in cystic fibrosis lung infections and possibly develop a therapy which involves inducing or boosting the response of the lung macrophage to Pseudomonas aeruginosa.

It is known that strains of P. aeruginosa from patients with cystic fibrosis are susceptible to phagocytosis by human neutrophils and macrophages in the absence of serum opsonins (5).

SUMMARY OF THE INVENTION

It is a purpose of the present invention to develop a feasible strategy for treating or preventing Pseudomonas aeruginosa infections.

The inventors have demonstrated that the macrophage receptor for unopsonized P. aeruginosa is dependent upon the presence of D-glucose for ingestion of P. aeruginosa by the macrophage. In the absence of glucose, phagocytosis of nonopsonized P. aeruginosa does not occur. This finding is in contrast to what has been observed with the other better characterized phagocytic receptors. It has previously been shown that glucose is present in diminishingly low concentrations in the lung which can explain why cystic fibrosis patients are at high risk for succumbing to Pseudomonas aeruginosa infections. There are no methods currently available that enhance lung macrophage function in patients with CF.

Accordingly, it is an aspect of the present invention to provide a pharmaceutical composition for treating or preventing Pseudomonas aeruginosa infections, which comprises as active ingredient D-glucose or D-mannose in admixture with a pharmaceutically acceptable carrier.

It is also an aspect to provide a method of treating or preventing infection by Pseudomonas aeruginosa which comprises administering to a patient in need of such a treatment an effective dose of a pharmaceutical composition comprising as active ingredient D-glucose or D-mannose in admixture with a pharmaceutically acceptable diluent or carrier.

It is another aspect to provide an aerosol delivery system containing a pharmaceutical composition comprising D-glucose or D-mannose as active ingredient in admixture with a pharmaceutically acceptable, liquid normally gaseous carrier.

DETAILED DESCRIPTION OF THE DRAWINGS

Figure 1A:
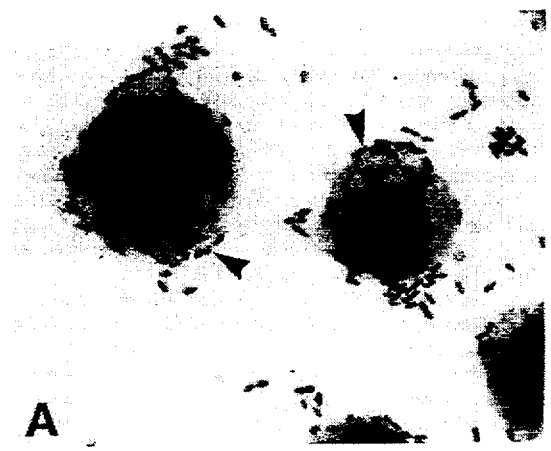
FIGS. 1(A, B, C, D, E and F) show the effect of glucose on phagocytosis of unopsonized Pseudomonas aeruginosa and unopsonized zymosan by thioglycollate-elicited mouse peritoneal macrophages.

*nosa* bound to the surface of murine peritoneal macrophages in the absence of glucose.

FIG. 4(A, B, C, and D) are transmission electron micrographs demonstrating phagocytosis of unopsonized *Pseudomonas aeruginosa* by murine peritoneal macrophages.

DETAILED DESCRIPTION OF THE INVENTION

The experimental data supporting the finding that phagocytosis of *Pseudomonas aeruginosa* by macrophages is dependent upon glucose is detailed below.

MATERIALS AND METHODS

Particles for Phagocytosis

*P. aeruginosa* strain P-1 is a nonmucoid derivative of a mucoid cystic fibrosis isolate (5). It has a rough lipopolysaccharide, is susceptible to the bactericidal effect of human serum and has from one to three polar pili per bacterium (6). It was grown overnight under static conditions in L broth [10 g tryptone (Difco, Detroit, Mich.), 5 g yeast extract (Difco) and 10 g NaCl per liter distilled water] and frozen in aliquots at $-70°$ C. Bacteria for each experiment were inoculated 1:100 from frozen stock in L broth and grown overnight under static conditions at 37° C. Immediately prior to use in phagocytosis experiments, the bacteria were gently vortexed to disrupt the pellicle and used without washing. Phagocytosis was usually assessed with unopsonized bacteria. Opsonization for some experiments was performed by tumbling the bacteria for 15 min. in one to five percent heat-inactivated (56° C. for 30 min) hyperimmune polyclonal rabbit serum. After opsonization, the bacteria were washed once and resuspended in phosphate-buffered saline, pH 7.4 (PBS).

Unopsonized zymosan, erythrocytes opsonized with IgG [EIgG and erythrocytes opsonized with IgM and complement [E(IgM)C] were prepared exactly as described (7).

Hyperimmune Anti-Pseudomonas Rabbit Serum

Hyperimmune serum was produced by repeatedly immunizing two adult New Zealand white rabbits with Formalin-killed *P. aeruginosa* strain P-1.

Phagocytic Cells

Phagocytic cells were obtained from the peritonea of mature female BALB/c mice. Leukocytes were elicited by intraperitoneal injection of one ml. Brewer's complete thioglycollate broth (8). Cells harvested one day later were approximately 70% neutrophils, whereas those harvested after three to six days were approximately 70 percent M$\phi$s. Resident cells consisted mainly of lymphocytes and about 25 percent M$\phi$s. Pulmonary alveolar macrophages were lavaged from freshly exsanguinated mature female BALB/c mice after intratracheal instillation of 1–2 ml. PBS with 0.4% lidocaine.

Reagents

L-glucose, D- and L-mannose, $\alpha$ lactose, D- and L-fucose, fructose, maltose and mannan were purchased from Sigma Chemicals, St. Louis, Mo. D-glucose, 2-deoxy-D-glucose, sucrose and Formalin were purchased from BDH, Toronto, Ontario and tobramycin was from Eli Lilly, Toronto. $\beta$lactose was from Eastman Kodak, Rochester, N.Y. and pyruvate was from Gibco, Grand Island, N.Y. Monoclonal antibody 5C6 is against the alpha chain of complement receptor 3 (9).

Cell culture media were prepared by the Terry Fox Laboratory (Vancouver, B.C.). Leibovitz's medium (L15) contained D(+) galactose (900 mg/L) as the carbon source. To the L15 medium was added 10 mM HEPES. Dulbecco's modified minimal essential medium (DMEM) and Hank's balanced salt solution (HBSS) were prepared without glucose. RPMI 1640 medium (with 11 mM D-glucose) was prepared in the standard manner.

Phagocytosis

Mice were killed with $CO_2$ or by exsanguination, and peritoneal or pulmonary alveolar cells were lavaged with PBS. Leukocytes were then washed in PBS, adjusted to approximately $4 \times 10^5$/ml in RPMI and 50 $\mu$L was loaded onto acid-washed 11 mm diam. round glass coverslips. The coverslips were incubated at 37° C. in 5% $CO_2$ and dipped several times in PBS to remove nonadherent cells. Peritoneal cells were used fresh and pulmonary cells were incubated overnight in 5% $CO_2$ before use. The coverslips were then added to duplicate 24-well plastic tissue culture plates (Becton Dickinson, Lincoln Park, N.J.) in which each well containing 400 $\mu$L of the medium in which the phagocytosis assay was to be performed. The plates were incubated at room temperature in ambient $CO_2$ for 30 minutes. After this period of equilibration, 40 $\mu$L of bacteria (prepared as described above) were added to each of the wells. The plates were incubated at 37° C. at ambient $CO_2$ for 60 minutes after which the coverslips were washed by gently injecting and aspirating one ml PBS six times. Methanol was then added to all wells of one of the duplicate plates and the coverslips contained therein were assessed for total bacteria bound and ingested. Wells in the other plate were treated as follows to lyse all uningested bacteria: The plate was chilled on ice and 500 $\mu$L ice-cold lysozyme (5 mg/ml; Sigma) in 0.25M TRIS buffer, pH 8.0 was added to each well. The plates were further incubated on ice for five minutes and then the wells washed with PBS. Finally, bacterial spheroplasts were lysed by adding 500 $\mu$L ice-cold distilled water for two min and the cover-slips were washed with PBS and fixed with methanol. The cover-slips were air-dried, mounted on glass microscope slides and stained with toluidine blue (one percent in one percent borax). In some experiments, the bacteria were centrifuged onto the M$\phi$s for seven minutes at 1500 $\times$g at room temperature immediately after the addition of bacteria to the wells.

Intraperitoneal neutrophils were obtained from mice one day after thioglycollate broth injection. The cells were washed, resuspended in HBSS with 0.1% gelatin (gHBSS) and mixed in a ratio of one neutrophil to 10 bacteria in four ml polypropylene snap top tubes (Falcon). The mixture was tumbled end over end for one hour at 37° C. and the uningested bacteria removed by three washes in gHBSS with centrifugation (168 $\times$g). The washed neutrophils were deposited on glass slides by cytocentrifugation (cytospin 2, Shandon, Sewickley, Pa.), air-dried overnight and stained with crystal violet.

Phagocytosis and binding were assessed by bright-field microscopy as described previously (10). Total ingested and bound bacteria were all those associated with leukocytes. Ingested bacteria were only those associated with leukocytes after lysozyme treatment.

Electron Microscopy

Transmission Electron Microscopy

Resident peritoneal Mφs ($10^7$) were mixed with *P. aeruginosa* ($3 \times 10^8$) in a volume of three ml L 15 medium (with or without 10 mM D-glucose) in 15 ml conical polypropylene tubes. The phagocytosis mixture was rotated for different periods of time, washed twice with PBS and fixed with 2.5% glutaraldehyde in 0.1M cacodylate buffer as described (1 1). The specimen was dehydrated with graded concentrations of ethanol, sectioned and viewed with a JEOL 100 CX electron microscope (JEOL, London, England) operating at 80 kV.

Scanning Electron Microscopy

Approximately $3 \times 10^5$ Mφs were plated on each of several glass chips and bacteria added as described above for assessment of phagocytosis. After appropriate incubations in L15 medium (with or without 10 mM D-glucose), the monolayer was washed with PBS and fixed with 2.5% glutaraldehyde in 0.1M cacodylate buffer. Specimens were prepared as described (11 ) and viewed with a JEOL 100 CX electron microscope with ASID scanning attachment operating at 40 kV.

Statistics

Differences were analyzed by a two-tailed student's t-test. A P value of $<0.05$ was considered statistically significant.

RESULTS

Figure 1B:
Figure 1C:
Figure 1D:
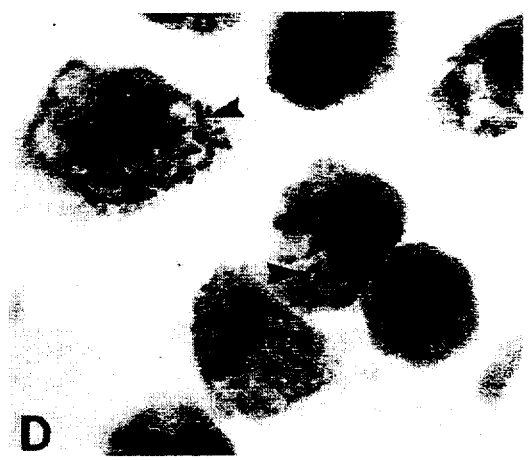
Figure 1E:
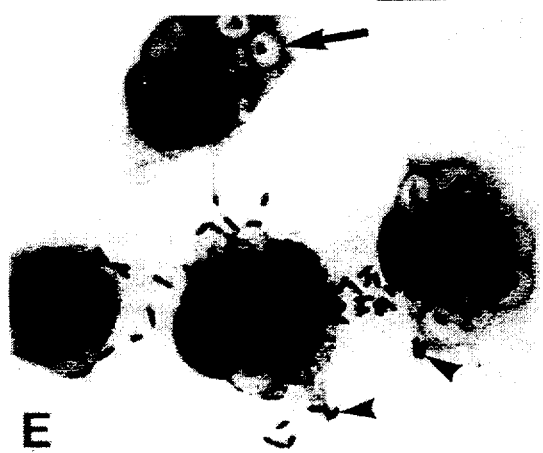
Figure 1F:

A. Glucose Requirement for Phagocytosis of Unopsonized *P. aeruginosa* by macrophages When Mφ were incubated with unopsonized *P. aeruoinosa* in L15, a medium that contains galactose rather than glucose, we noticed that the bacteria were bound but not ingested. FIG. 1A demonstrates bacteria bound to thioglycollate-elicited murine peritoneal Mφs. After lysozyme treatment (FIG. 1C), bacteria were only rarely seen associated with the Mφs. When RPMI 1640 medium (that contains glucose) was substituted for L15, phagocytosis was clearly evident (data not shown). In order to determine the phagocytosis-promoting factor in RPMI 1640 that was absent from L15, additional experiments were performed. When D-glucose was added, phagocytosis was enhanced in a dose-dependent fashion (FIG. 2), with 10 mM the optimum concentration. All subsequent experiments were therefore performed with 10 mM D-glucose. Glucose promoted ingestion of all ten additional *P. aeruginosa* strains examined (data not shown). Bacteria which were phagocytosed in the presence of glucose (FIG. 1B) were resistant to lysozyme-mediated lysis (FIG. 1D). Glucose selectively promoted uptake of unopsonized *P. aeruginosa*. Phagocytosis of unopsonized zymosan occurred even if unopsonized *P. aeruginosa* was added, both in the absence (FIG. 1E) and presence (FIG. 1F) of 10 mM D-glucose.

Figure 3A:
FIG. 3(A, B, C, and D) are scanning electron micrographs demonstrating unopsonized Pseudomonas aerugi-
Figure 3B:
Figure 3C:
Figure 3D:

Ultrastructural studies were performed to explore more fully the process by which glucose promoted nonopsonic phagocytosis. Bacteria which bound to the Mφ surface in the absence of glucose elaborated filamentous structures that were clearly seen by scanning electron microscopy (FIGS. 3 A,B). These filaments appeared to be peritrichal rather than polar. The expression of these unusual structures was independent of glucose and was also observed when bacteria were plated on glass. The structures extended both among bacteria and between bacteria and Mφs, and they appeared to be of bacterial origin. Some bound bacteria were nestled among pseudopodia (FIG. 3C), and after glucose was added were observed partially obscured within collar-like Mφ structures (FIG. 3D).

Figure 4A:
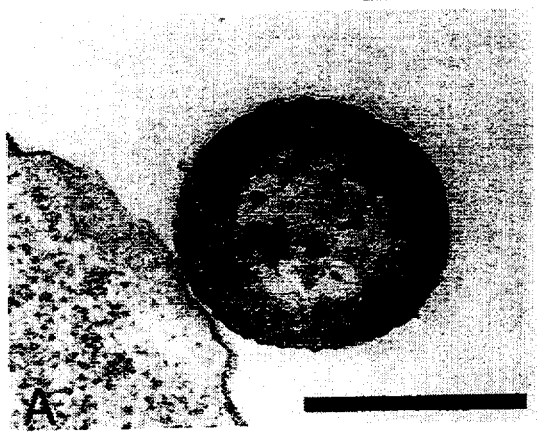
Figure 4B:
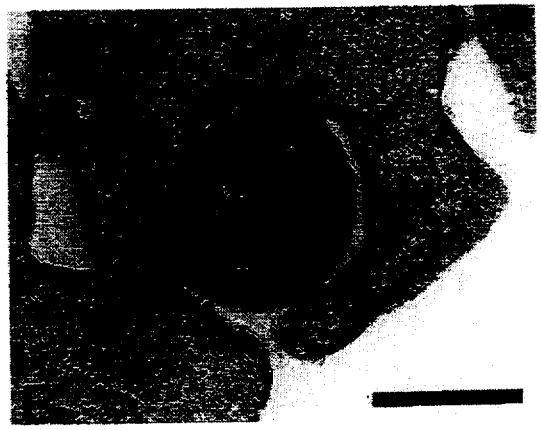
Figure 4C:
Figure 4D:

Mφs were fully viable after incubation with or without D-glucose. Electron microscopic examination demonstrated that unopsonized *P. aeruginosa* entered Mφs in a "zippering-like" manner whereby pseudopodia engulfed the bacteria by spreading circumferentially around their surfaces. (FIG. 4). Bacteria were bound to the Mφ surface in the absence of glucose (FIG. 4A) and then were engulfed within pseudopodia after the addition of glucose (FIG. 4B). Phagocytosed bacteria were subsequently observed singly (FIG. 4C) or multiply (FIG. 4D) within phagosomes.

The requirement for glucose for the phagocytosis of *P. aeruginosa* was also observed in human macrophages including peritoneal macrophages, pulmonary alveolar macrophages and blood or monocyte-derived macrophages.

B. The Ability of Other Sugars to Substitute for D-glucose

Figure 2:
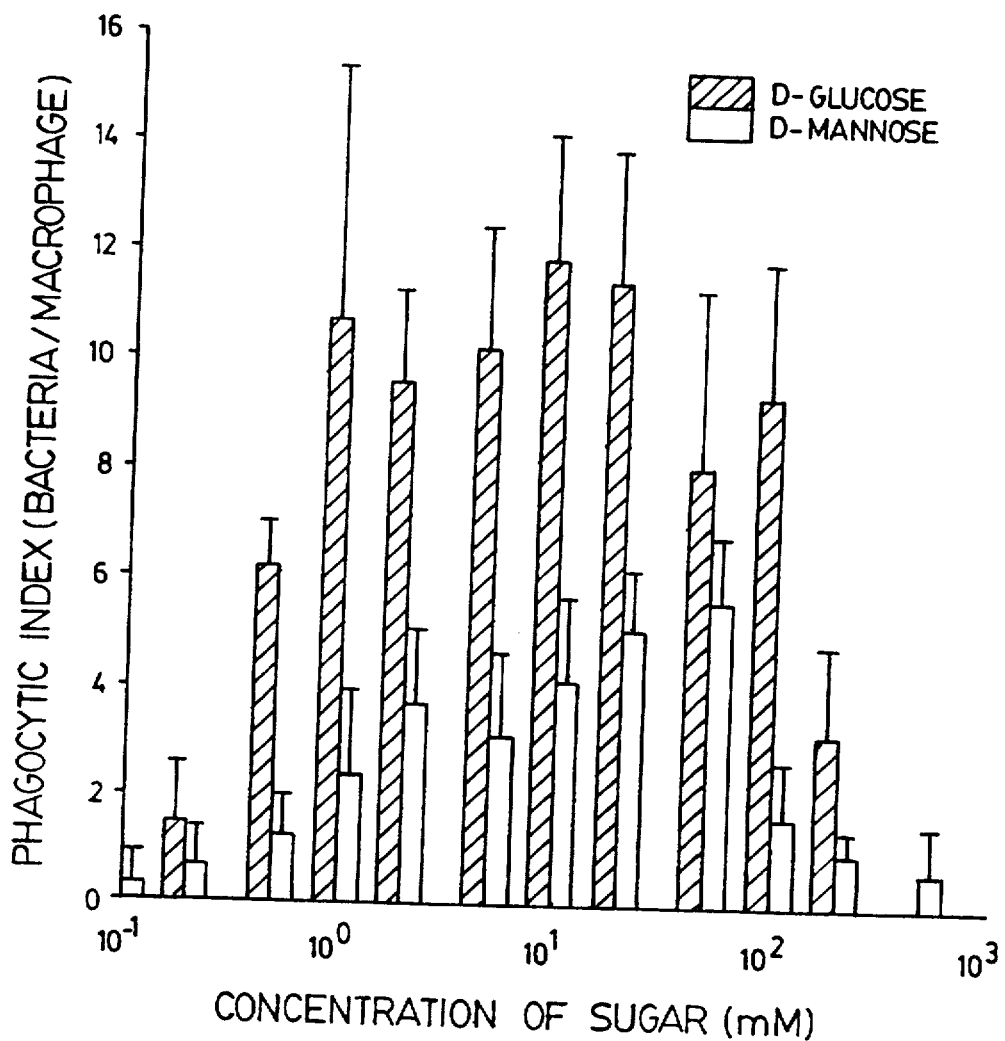
FIG. 2 illustrates the effect of varying concentrations of D-glucose and D-manose on phagocytosis of unopsonized Pseudomonas aeruginosa by macrophages.

D-mannose was the only saccharide found that could substitute for D-glucose to enhance phagocytosis of unopsonized *P. aeruginosa* (Table 1). A dose-dependent enhancing effect was seen (FIG. 2). The optimum concentration for D-mannose was 50 mM (approximately five-fold higher than for D-glucose), and even at that concentration was substantially less able than glucose to augment phagocytosis (FIG. 2). Other sugars, including 2-deoxyglucose and L stereoisomers of both glucose and mannose were unable to enhance phagocytosis. Glucose was required for phagocytosis of unopsonized *P. aeruginosa* whether performed in L15, DMEM or HBSS medium (Table 1). If *P. aeruginosa* were bound to Mφs in the absence of glucose, phagocytosis was first seen approximately 15 minutes after the addition of 10 mM D-glucose (data not shown).

C. Functional Characterization of the Macrophage Receptors for Binding and Phagocytosis of Unopsonized *P. aeruginosa*

Mannan (10 mg/ml) and antibody to complement receptor 3 (5C6, 40 μg/ml) did not inhibit phagocytosis of *P. aeruginosa* although active in controls (data not shown). Therefore the murine Mφ receptor for phagocytosis of unopsonized Pseudomonas appeared to be neither CR3 nor the mannosyl/fucosyl receptor.

Bacterial viability appeared to be necessary for binding to Mφs (Table 2). If *P. aeruginosa* was killed by heat (56° C.×30 min) or by Formalin, neither binding nor ingestion in the presence or absence of D-glucose was observed. Mφ viability was required for ingestion but not for binding of unopsonized *P. aeruginosa*. If the monolayer was fixed with methanol, bacteria bound to the Mφs in the presence or absence of glucose, but ingestion did not occur. Phagocytosis appeared to be temperature-dependent, since binding was reduced and ingestion did not occur at 4° C. This inhibition of binding at 4° C. could have been due to decreased bacterial motility, a characteristic of flagellated *P. aeruginosa* which appears to be temperature-dependent.

D. Role of Bacterial Viability in Glucose-Dependent Phagocytosis

Experiments were performed to determine if the glucose was acting on the bacteria or the Mφ. Since bacterial viability appeared to be necessary for binding to occur, it was necessary to devise an experiment in which the bacteria were killed after binding to the Mφ membrane. An agent was required that had specific effects on the bacteria without interfering with viability and function of the Mφ. Unopsonized *P. aeruginosa* were bound to Mφs for 45 min in the absence of D-glucose. Tobramycin (20 μg/ml) was then added for 60 min. This treatment killed over 99% of the bacteria. After the monolayer was washed with PBS, 10 mM D-glucose was added. Phagocytosis of unopsonized *P. aeruginosa* was observed whether the bacteria were killed with tobramycin (3.9 bacteria/Mφ) or remained viable (5.3). The difference in phagocytosis between these two conditions was not statistically significant (P>0.05). However, phagocytosis of both live and killed bacteria in the presence of glucose significantly exceeded ingestion in its absence (P<0.001 for each comparison). This experiment suggested that the glucose promoted phagocytosis by effects on the Mφ.

Another experiment was performed to confirm that glucose was acting on the Mφ rather than the bacteria. (Table 3). Bacteria were killed with Formalin, washed and then centrifuged onto coverslips upon which Mφs had been plated. Phagocytosis of both live and Formalin-killed bacteria was substantially enhanced in the presence of glucose. Whereas live bacteria were well-ingested with or without centrifugation, Formalin-killed bacteria were ingested only when centrifuged onto the Mφs.

Finally, *P. aeruginosa* were grown in L-broth supplemented with 10 mM D-glucose. When the bacteria were added to the L15 phagocytosis buffer, the glucose was diluted to 0.5 mM and phagocytosis was not facilitated (data not shown). This further suggested that the glucose was not inducing elaboration of a phagocytosis-promoting ligand on the bacteria.

E. Effect of D-glucose on Phagocytosis of Unopsonized *Pseudomonas aeruginosa* by Different Phagocytic Cells Resident and thioglycollate-elicited peritoneal and pulmonary alveolar Mφs from BALB/c mice ingested unopsonized *P. aeruginosa* to a similar extent, but both required D-glucose (Table 4). The same was true for biogel-elicited peritoneal and bone marrow-derived Mφs from BALB/c mice and peritoneal Mφs from C57 mice (data not shown). Although those diverse Mφ phenotypes were all dependent upon glucose for phagocytosis, murine neutrophils were able to bind and ingest unopsonized *P. aeruginosa* in the absence of added sugar (Table 5).

F. Enhancement of Phagocytosis by D-glucose was Specific for *P. aeruginosa*

Unopsonized *P. aeruginosa* was the only particle tested which was not ingested by peritoneal Mφs in the absence of D-glucose (Table 5). Phagocytosis of unopsonized zymosan E(IgM)C's and EIgG's was equivalent in the absence and presence of the sugar. When *P. aeruginosa* was opsonized with polyclonal rabbit serum, phagocytosis occurred in the presence of absence of glucose. The enhanced phagocytosis in the presence of glucose could have reflected the combined activities of both opsonic and nonopsonic receptors.

G. Mechanism of Glucose-Dependency

The glucose dependency for ingestion by macrophages is mediated by an active transport of glucose into the macrophage by a sodium-dependent glucose transporter. This transport is facilitated in the presence of sodium and an active chloride channel. Phlorizin, a specific inhibitor of sodium-dependent glucose transport, inhibits the phagocytosis of *Pseudomonas aeruginosa* by macrophages. In particular, the investigators have shown that 1.5 mM of phlorizin inhibits phagocytosis by 75% and 5 mM of phlorizin inhibits phagocytosis by 73.5%. In one experiment, macrophages were pre-treated with phlorizin and washed before being incubated with *Pseudomonas aeruginosa*. No phagocytosis was observed. In another experiment, the *Pseudomonas* was pre-treated with phlorizin, washed and then incubated with macrophages. Phagocytosis was observed. These experiments confirm that the sodium dependent glucose transporter is on the macrophage. Substitution of potassium for sodium was also shown to inhibit phagocytosis of *Pseudomonas aeruginosa* but had no effect on the phagocytosis of unopsonized zymosan, illustrating once more that the observed phenomenon is peculiar to *Pseudomonas aeruginosa*, and further indicating a role for a sodium dependent glucose transport system.

SUMMARY

In view of all of the above, it appears that the means by which glucose enhances phagocytosis of unopsonized *P. aeruginosa* is by acting on the Mφ rather than the bacteria. This conclusion is based on the following evidence: (i) although Mφs required glucose for phagocytosis of *Pseudomonas*, PMNs were fully competent to ingest in the absence of glucose; (ii) if bacteria killed by tobramycin or heat were bound to Mφs, glucose facilitated their ingestion; (iii) mannose was the only sugar identified so far which is able to substitute for glucose in promoting phagocytosis; this is consistent with previous observations in which these were the only two monosaccharides able to reverse the inhibitory effects of 2-deoxyglucose (10), suggesting a specific energy-requiring event; (iv) growth of *P. aeruginosa* in a glucose-replete medium did not facilitate phagocytosis; and (v) pre-treatment of the macrophages, but not the bacteria, with phlorizin inhibited phagocytosis.

Observations from these studies provide novel insights into the mechanism by which macrophages ingest unopsonized *P. aeruginosa*. Phagocytosis of *Pseudomonas* appears to be unique in its dependence upon glucose, which was required for ingestion by macrophages but not by neutrophils. A clear two-step process was observed in which binding occurred independent of glucose or macrophage viability, and ingestion was dependent upon glucose but did not require bacterial viability.

Glucose-dependent ingestion appears to be specific for *P. aeruginosa* and was observed with ten different bacterial isolates (data not shown). Other Gram-negative bacterial species (including *Escherichia coli* and *Salmonella typhimurium*) were ingested equally well in the absence and presence of glucose (data not shown).

Complement receptor 3 (CR3) possesses some of the characteristics of the receptor-mediated phagocytic processes described in this patent application. Although CR3 is competent constitutively to bind particles coated with iC3b, ingestion only occurs if the M$\phi$s are exposed to agents such as phorbol esters or fibronectin (12,13). Whereas such observations indicate two steps in CR3-mediated ingestion, both appear to be mediated by a single type of receptor. Unlike phagocytosis by CR3, ingestion of unopsonized P. aeruginosa was unaffected by phorbol myristate acetate in the absence or presence of glucose or by antibody to CR3 (data not shown). Furthermore, resident peritoneal M$\phi$s were able constitutively to ingest unopsonized P. aeruginosa, whereas complement-coated particles are bound but not ingested under the same conditions.

A role for glucose in receptor-mediated phagocytosis has been investigated previously (14). Studies were performed in which 2-deoxyglucose interfered with ingestion but not binding by both Fc and complement receptors (14), unlike observations from the present studies in which these receptors performed normally in the absence of glucose. These investigators also found that 2-deoxy-D-glucose had no effect on the ingestion of two unopsonized particles (zymosan and latex). These results seem contrary to the present finding that phagocytosis of non-opsonized particles is glucose dependent i.e. one would expect a glucose inhibitor to inhibit phagocytosis of unopsonized particles. Michl and co-workers suggested that the 2-deoxyglucose exerted its inhibitory effects on the M$\phi$ rather than the phagocytosed particle but were unable to demonstrate its mechanism of action (15). A further series of investigations by Sung and Silverstein (16) suggested that 2-deoxyglucose did not inhibit phagocytosis by abrogating glycosylation, protein synthesis or energy stores.

Phagocytosis is an active process dependent upon recruitment of specific receptors to the plasma membrane. The mechanism by which glucose promotes this process with unopsonized P. aeruginosa remains to be determined. Glycolysis provides the energy required for phagocytosis (17), and glucose may serve as the necessary substrate. M$\phi$ hexokinase activity is very high relative to other cell types, suggesting that glucose is an important metabolic fuel (18). Alternatively, glycosylation of an essential membrane protein or lipid may be required for ingestion of unopsonized P. aeruginosa. Such a modification could be required to alter the functional state of a specific receptor or to permit transduction of a signal for facilitating the ingestion of a bound particle.

The investigators have recently found that the glucose-dependency for ingestion by macrophages is mediated by an active transport of glucose into the macrophage by a sodium-dependent glucose transporter. This transport is facilitated in the presence of sodium and an active chloride channel and is blocked by phlorizin (a specific inhibitor of sodium-dependent glucose transport). This raises the possibility that pharmacological manipulation of Pseudomonas ingestion by macrophages might be possible in patients with CF.

Nonopsonic phagocytosis by M$\phi$s may be critically important in defense of the lower respiratory tract against infection prior to the initiation of an inflammatory response with the attendant influx of neutrophils, complement and immunoglobulin. Bronchial fluid has diminishingly low levels of glucose present under normal conditions (19). The predilection of P. aeruginosa for lower airway disease in patients with cystic fibrosis might be explained in part by the unique dependency upon glucose for M$\phi$-mediated ingestion of this particular bacterial species.

The investigators have shown that human macrophages require glucose in order to phagocytose Pseudomonas aeruginosa in vitro. They and others have looked at macrophages derived from patients with cystic fibrosis and have determined that they appear to be functionally normal (20). Therefore, the administration of glucose to patients with cystic fibrosis to facilitate the phagocytic response of the lung macrophages to Pseudomonas aeruginosa and thereby prevent or combat this infection is a promising form of therapy for this disease. However, since established Pseudomonas aeruginosa infections in CF patients are rarely, if ever, eradicated, glucose therapy may be most useful as a prophylactic regimen for patients with cystic fibrosis. This therapy would be given before the infection is evident in order to prevent infection by Pseudomonas aeruginosa. Glucose is a benign non-toxic substance and therefore adverse reactions or side effects are not expected.

Since Pseudomonas aeruginosa infections occur in the endobronchial space of the lung, it is necessary to administer the glucose in a form that will effectively reach the airways. In general, delivery of therapeutic agents to the airways is effected by using an aerosol formulation that is administered by inhalation. Therefore, inhalation of an aerosol preparation containing glucose is the preferred mode of administration. An aerosolized glucose composition can be readily prepared by methods known in the art.

TABLE 1

Effect of simple sugars on phagocytosis of viable unopsonized Pseudomonas aeruginosa by macrophages

| Condition | | Ingested Bacteria/Macrophage* (

TABLE 2-continued

Effect of macrophage and bacterial viability and of temperature on binding and phagocytosis of unopsonized *Pseudomonas aeruginosa*

| | Bacteria/Macrophage | | | |
|---|---|---|---|---|
| | Without added glucose | | 10 mM D-glucose | |
| Condition | Ingested* | Bound & Ingested* | Ingested | Bound & Ingested |
| (56° C. × 30 min) Formatin-killed Bacteria | 0.3 | 0.2 | 0.3 | 0.5 |
| Methanol-fixed macrophages | 0 | 18.5 | 0 | 19.8 |
| Incubation at 4° C. | 0.7 | 2.9 | 0.4 | 52 |

*Ingested and Bound & Ingested were determined as described in Table 2.

TABLE 3

Bacterial viability is not required for glucose-induced phagocytosis of *Pseudomonas aeruginosa*

| Bacterial viability | Centrifuged onto macrophages | Ingested Bacteria/Macrophage* | |
|---|---|---|---|
| | | Without added glucose | 10 mM D-glucose |
| Viable | No | 0 | 13.5 |
| Viable | Yes | 0.4 | 25.1 |
| Formalin-killed | No | 2.5 | 1.8 |
| Formalin-killed | Yes | 1.6 | 7.1 |

*Macrophages were incubated with bacteria for 60 minutes and washed, after which uningested bacteria were lysed with lysozyme.
Bacteria were forced onto the monolayer by centrifugation at 1500 × g for seven minutes or were allowed to contact the monolayer without centrifugation.
Different from number of bacteria ingested in absence of added glucose (P < 0.001)

TABLE 4

Glucose is required for phagocytosis of unopsonized *Pseudomonas aeruginosa* by macrophages but not by neutrophils

| Phagocytic Cell | Ingested Bacteria/Macrophage* | |
|---|---|---|
| | without added glucose | 10 mM D-glucose |
| Resident Peritoneal Macrophage | 0.6 | 11.7 |
| Thioglycollate-elicited Peritoneal Macrophage | 2.2 | 10.9 |
| Pulmonary alveolar Macrophage | 0 | 7.6 |
| Thioglycollate-elicited Peritoneal Neutrophil | 7.1 | 7.2 |

*Macrophages were incubated with bacteria for 60 minutes and washed, after which uningested bacteria were lysed with lysozyme.
Different from number of bacteria ingested in the absence of added glucose (P < 0.001)

TABLE 5

Glucose is required selectively for phagocytosis of *Pseudomonas aeruginosa*

| Particle | Particles/Macrophage* | |
|---|---|---|
| | Without Added Glucose | 10 mM D-glucose |
| Unopsonized P. aeruginosa | 0 | 10.7 |
| Opsonized P. aeruginosa | 82 | 18.1 |
| Unopsonized zymosan | 7.7 | 7.0 |
| E IgG | 4.6 | 53 |
| E(IgM)C | 2.4 | 3.5 |

*Data represent mean number of particles ingested per macrophage except for E(IgM)C in which particles bound per macrophage was determined.
Different from number of bacteria ingested in the absence of added glucose (P < 0.001)

REFERENCES

1. Wilmott R. W., Tyson S. L., Matthew D. J. Cystic fibrosis survival rates. Am. J. Dis. Child. 1985; 139:669–671.
2. Wood R. E., Boat T. F., Doershuk C. F. Cystic fibrosis. Am. Rev. Respir. Dis. 1976; 113:833–878.
3. Auerbach H. S., Williams M, Kirkpatrick J. A., Colten H. R. Alternate-day prednisone reduces morbidity and improves pulmonary function in cystic fibrosis. Lancet. 1985; Sept. 28:686–688.
4. Rosenstein B. J., Eigen H. Risks of alternate-day prednisone in patients with cystic fibrosis. Pediatr. 1991; 87:245–246.
5. Speert, D. P., F. Eftekhar and M. L. Puterman. 1984. Non-opsonic phagocytosis of strains of *Pseudomonas aeruginosa* from cystic fibrosis patients, Infect. Immun. 43:1006–1011.
6. Speert, D. P., B. A. Loh, D. A. Cabral, and I. E. Salit. 1986. Nonopsonic phagocytosis of nonmucoid *Pseudomonas aeruginosa* by human neutrophils and monocyte-derived macrophages is correlated with bacterial piliation and hydrophobicity, Infect. Immun. 53:207–12.
7. Cabral, D. A., B. A. Loh, and D. P. Speert. 1987. Mucoid *Pseudomonas aeruginosa* resists nonopsonic phagocytosis by human neutrophils and macrophages, Pediatr. Res. 22:429–431.
8. Johnston, R. B. Jr., C. A. Godzik, and Z. A. Cohn. 1978. Increased superoxide anion production by immunologically activated and chemically elicited macrophages, J. Exp. Med. 148:115–127.
9. Rosen, H., and S. Gordon. 1987. Monoclonal antibody to the murine type 3 complement receptor inhibits adhesive of myelomonocytic cells in vitro and inflammatory cell recruitment in vivo. J. Exp. Med. 166:1685–1701.
10. Speert, D. P., S. D. Wright, S. C. Silverstein, and B. Mah. 1988. Functional characterization of human macrophage receptors for in vitro phagocytosis of unopsonized Pseudomonas aeruginosa, J. Clin. Invest. 82:872–879.
11. Ezekowitz, R. A. B., R. B. Sim, G. G. MacPherson, and S. Gordon. 1985. Interaction of human monocytes, macrophages, and polymorphonuclear leukocytes with zymosan in vitro: role of type 3 complement receptors and macrophage-derived complement, J. Clin. Invest. 76:2368–2376.
12. Wright, S. D. and S. C. Silverstein. 1982. Tumor-promoting phorbol esters stimulate C3b and C3b' receptor-mediated phagocytosis in cultured human monocytes, J. Exp. Med. 156:1149–1164.
13. Wright, S. D., L. S. Craigmyle, and S. C. Silverstein. 1983. Fibronectin and serum amyloid P component stimulate C3b and C3bi-mediated phagocytosis in cultured human monocytes, J. Exp. Med. 158:1338–1343.
14. Michl, J., D. J. Ohlbaum, and S. C. Silverstein. 1976. 2-deoxyglucose selectively inhibits Fc and complement receptor-mediated phagocytosis in mouse peritoneal macrophages. I. Description of the inhibitory effect, J. Exp. Med. 144:1465–1483.
15. Michl, J., D. J. Ohlbaum, and S. C. Silverstein. 1976. 2-deoxyglucose selectively inhibits Fc and complement receptor-mediated phagocytosis in mouse peritoneal macrophages. II. dissociation of the inhibitory effects of 2-deoxyglucose on phagocytosis and ATP generation, J. Exp. Med. 144:1484–1493.

16. Sung, S. J., and S. C. Silverstein. 1985. Role of 2 2-deoxy-glucose in the inhibition of phagocytosis by mouse peritoneal macrophages. *Biochem. Biophys. Acta.* 845:204–215.

17. Silverstein, S. C., S. Greenberg, F. Di Virgilio, and T. H. Steinberg. 1989. Phagocytosis, in "Fundamental Immunology", (Paul, W. E. ed.) pp. 703–720, Raven Press, New York.

18. Newsholme, P., R. Curi, S. Gordon, and E. A. Newsholme. 1986. Metabolism of glucose, glutamine, long-chain fatty acids and ketone bodies by murine macrophages. *Biochem. J.* 239:121–125.

19. Valeyre, D., P. Soler, G. Bassert, P. Loiseau, J. Pre, P. Turbie, J. P. Battesti, and R. Georges. 1991. Glucose, $K^+$, and albumin concentrations in the alveolar milieu of normal humans and pulmonary sarcoidosis patients, *Am. Rev. Resp. Dis.* 143:1096–1101.

20. Speert, D. P. 1985. Host defences in cystic fibrosis: Modulation by *Pseudomonas aeruginosa*. *Survey and Synthesis of Pathology Research.* 4:14–33.

What we claim as our invention is:

1. A method of treating or preventing infection by *Pseudomonas aeruginosa* in a person with cystic fibrosis which comprises administering to said person an effective dose of a pharmaceutical composition comprising, as an active ingredient, D-glucose or D-mannose in admixture with a pharmaceutically acceptable diluent or carrier.

2. The method according to claim 1 wherein said carrier is a liquified normally gaseous carrier.

3. The method according to claim 1 wherein said active ingredient is D-glucose.

4. A method according to claim 3 wherein said D-glucose is present in a final concentration of from about 5 mM to about 10 mM.

5. A method according to claim 1 wherein said composition is a pulmonary aerosol and is administered by inhalation.

* * * * *